United States Patent
Koerth et al.

(10) Patent No.: US 9,770,378 B2
(45) Date of Patent: Sep. 26, 2017

(54) DOCKING APPARATUS

(71) Applicants: Michael Koerth, Fürth (DE); Matthias Müller, Kemnath (DE); Kerstin Waldbach, Porstendorf (DE)

(72) Inventors: Michael Koerth, Fürth (DE); Matthias Müller, Kemnath (DE); Kerstin Waldbach, Porstendorf (DE)

(73) Assignee: Siemens Aktiengesellschaft, München (DE)

(*) Notice: Subject to any disclaimer, the term of this patent is extended or adjusted under 35 U.S.C. 154(b) by 535 days.

(21) Appl. No.: 14/273,853

(22) Filed: May 9, 2014

(65) Prior Publication Data
US 2014/0335734 A1 Nov. 13, 2014

(30) Foreign Application Priority Data

May 10, 2013 (DE) .................. 10 2013 208 650

(51) Int. Cl.
*A61G 7/05* (2006.01)
*A61G 13/10* (2006.01)
(Continued)

(52) U.S. Cl.
CPC .................. *A61G 7/05* (2013.01); *A61G 1/02* (2013.01); *A61B 5/055* (2013.01); *A61B 6/0407* (2013.01); *A61G 13/10* (2013.01); *A61G 2203/80* (2013.01)

(58) Field of Classification Search
CPC .......... A61G 1/04; A61G 7/05; A61G 7/1046; A61G 13/10; A61G 2210/50; A61B 6/04;
(Continued)

(56) References Cited

U.S. PATENT DOCUMENTS

| 4,567,894 A | * | 2/1986 | Bergman | A61B 5/0555 403/325 |
| 4,727,328 A | * | 2/1988 | Carper | A61B 6/0442 324/318 |

(Continued)

FOREIGN PATENT DOCUMENTS

| CN | 1585620 A | 2/2005 |
| CN | 1895175 A | 1/2007 |

(Continued)

OTHER PUBLICATIONS

German Office Action dated Jan. 10, 2014 in corresponding German Patent Application No. DE 10 2013 208 650.4 with English translation.
(Continued)

*Primary Examiner* — Robert G Santos
(74) *Attorney, Agent, or Firm* — Lempia Summerfield Katz LLC

(57) ABSTRACT

A transportation apparatus configured to dock with a device to which power is supplied is provided. The transportation apparatus includes a first contact element for establishing a first contact with the device and a second contact element for establishing a second contact with the device. An apparatus for assisting in establishing the contact between the second contact element and the device is further provided in the transportation apparatus. The apparatus is operated by a motor. The apparatus is configured to provide power to the motor by supplying power via the first contact.

13 Claims, 4 Drawing Sheets

(51) Int. Cl.
  *A61B 5/055* (2006.01)
  *A61B 6/04* (2006.01)
  *A61G 1/02* (2006.01)

(58) Field of Classification Search
  CPC ..... A61B 6/0407; A61B 6/0457; A61B 5/055; A61B 5/0555
  USPC ....... 5/601, 600, 620, 86.1, 81.1 R; 378/208, 378/209
  See application file for complete search history.

(56) References Cited

U.S. PATENT DOCUMENTS

| | | | |
|---|---|---|---|
| 5,525,905 A * | 6/1996 | Mohapatra | A61B 6/0457 324/318 |
| 6,640,364 B1 | 11/2003 | Josephson et al. | |
| 6,895,715 B2 | 5/2005 | Gallant et al. | |
| 6,973,689 B2 * | 12/2005 | Lenting | A61B 6/0457 378/209 |
| 7,884,735 B2 | 2/2011 | Newkirk | |
| 7,986,141 B2 | 7/2011 | Feld et al. | |
| 8,132,276 B2 * | 3/2012 | Klemm | A61B 5/0555 378/209 |
| 9,248,061 B2 * | 2/2016 | Koerth | A61G 1/02 |
| 9,549,687 B2 * | 1/2017 | Georgiev | A61B 5/0555 |
| 9,592,024 B2 * | 3/2017 | Iizuka | A61B 5/0555 |
| 2005/0020906 A1 * | 1/2005 | Seijger | A61B 6/0457 600/415 |
| 2005/0034237 A1 * | 2/2005 | Lenting | A61B 6/0457 5/600 |
| 2006/0167356 A1 | 7/2006 | Everett et al. | |
| 2007/0020070 A1 | 1/2007 | Venkatachalapathy | |
| 2008/0014161 A1 | 1/2008 | Samain et al. | |
| 2008/0141461 A1 * | 6/2008 | Feld | A61B 5/0555 5/601 |
| 2010/0031443 A1 | 2/2010 | Georgiev et al. | |
| 2011/0067179 A1 * | 3/2011 | Klemm | A61B 5/0555 5/601 |
| 2014/0296692 A1 * | 10/2014 | Iizuka | A61B 5/0555 600/407 |
| 2014/0335734 A1 * | 11/2014 | Koerth | A61G 7/05 439/626 |
| 2014/0357981 A1 * | 12/2014 | Dumoulin | A61B 5/0555 600/415 |
| 2014/0359942 A1 * | 12/2014 | Koerth | A61G 1/02 5/611 |
| 2015/0272518 A1 * | 10/2015 | Koerth | A61B 6/0407 5/601 |

FOREIGN PATENT DOCUMENTS

| | | |
|---|---|---|
| CN | 101194837 A | 6/2008 |
| CN | 102028495 A | 6/2008 |
| CN | 101491901 A | 7/2009 |
| DE | 102010041314 | 3/2012 |
| DE | 102010041323 | 3/2012 |

OTHER PUBLICATIONS

Chinese office Action for related Chinese Application No. 201410195238.4 dated Jun. 3, 2016, with English Translation.
Chinese office Action for related Chinese Application No. 201410195238.4 dated Apr. 14, 2017, with English Translation.

* cited by examiner

DOCKING APPARATUS

This application claims the benefit of DE 10 2013 208 650.4, filed on May 10, 2013, which is hereby incorporated by reference in its entirety.

BACKGROUND

The present embodiments relate to docking between a transportation apparatus and a device having an interface for docking.

Docking or connecting a transportation apparatus to a device plays a role, for example, in medical technology. In this field, patient transportation apparatuses (e.g., trolleys) are to be docked or electrically and mechanically connected to a medical device (e.g., a magnetic resonance tomography scanner) in order to assist a movement of the patient from the patient transportation apparatus onto or into the medical device. Docking a patient transportation apparatus sometimes requires a considerable expenditure of force and a certain level of skill. Carrying out the docking process efficiently is important for providing fluid medical workflows and good patient throughput.

US 2006/0167356 A1 discloses a mechanism that assists the process of docking a patient transportation apparatus to a medical device. In this case, sensors and automatic assistance of the docking process are proposed.

SUMMARY AND DESCRIPTION

The scope of the present invention is defined solely by the appended claims and is not affected to any degree by the statements within this summary.

The present embodiments may obviate one or more of the drawbacks or limitations in the related art. For example, efficient assisting of docking with a low level of expenditure is provided.

In one embodiment, a transportation apparatus (e.g., a patient transportation apparatus) that is configured to dock with a device to which power is supplied is provided. The transportation apparatus includes a first contact element for establishing a first contact with the device, and a second contact element for establishing a second contact with the device. In this case, a plurality or a large number of contact elements may in each case be provided instead of one contact element. The transportation apparatus includes an apparatus for assisting in establishing the contact between the second contact element and the device. The transportation apparatus is operated by a motor. The apparatus is configured to provide power or supply power using the first contact. The first contact may include a plug contact, for example. Other contacts for transmitting power (e.g., using a slip ring or a capacitive coupling), however, may be provided.

Since the apparatus for assisting in establishing the contact draws power via the first contact, establishment of the second contact (e.g., a large number of second contacts) may be assisted by motor without a separate power supply being required for this purpose in the moving device. This results in a low-expenditure solution for assisting in establishing a contact between a transportation apparatus and a device to which power is supplied.

The assistance in establishing the second contact may be realized in the form of a movement or transportation of the second contact element in the direction of the device. The apparatus for assisting in establishing the contact may include a linear guide for this purpose.

In one embodiment, the transportation apparatus includes two states: a state in which the second contact element is extended in the direction of the device (e.g., docking state); and a state in which the second contact element is retracted (e.g., movement state). This second state (e.g., the movement state) may also be assumed again after the transportation apparatus has undocked from the device.

The two different states may be realized by the first contact element being arranged, in the movement state of the transportation process, such that the first contact element is offset in relation to the second contact element such that, during a docking process, the first contact element makes contact with the device without contact being made between the second contact element and the device. The second contact would then be established only with the assistance of the apparatus that is operated by the motor.

According to one embodiment, the transportation apparatus is additionally configured for a mechanical connection that may be established in the movement state. This additional mechanical connection provides a relatively high degree of stability when establishing the second contact. The additional mechanical connection may be made virtually at the same time as the first contact is established. In another embodiment, the additional mechanical connection is triggered or initiated by the first contact being established.

In one embodiment, a device having an interface for docking a transportation apparatus is also provided. The interface includes a first contact element and a second contact element. The device is configured to transmit power to the transportation apparatus via the first contact element. This device may be, for example, a medical diagnosis or therapy device (e.g., magnetic resonance tomography (MRT) scanner, computer tomography (CT) scanner, X-ray device, a tumor radiation device, an ultrasound device, etc.).

In one embodiment, a system including a transportation apparatus and a device according to the above description is provided.

A method for establishing a contact between a transportation apparatus and a device is also provided. The method includes establishing a first contact using first contact elements of the transportation apparatus and of the device. A motor of the transportation apparatus is supplied with power via the first contact. The motor serves to assist in establishing a second contact between contact elements of the transportation apparatus and of the device. This assistance may be performed such that a second contact element of the transportation apparatus is moved toward the device by the motor, for the purpose of making contact.

DETAILED DESCRIPTION

One option for, for example, specific magnetic resonance tomography or imaging systems (MRI systems) is a mobile hospital bed that may be undocked from the MRI system and may then be freely moved within a hospital. When the bed is redocked to the system, a large number of electrical connections between the bed and the system are to be established at the docking point.

Figure 1:
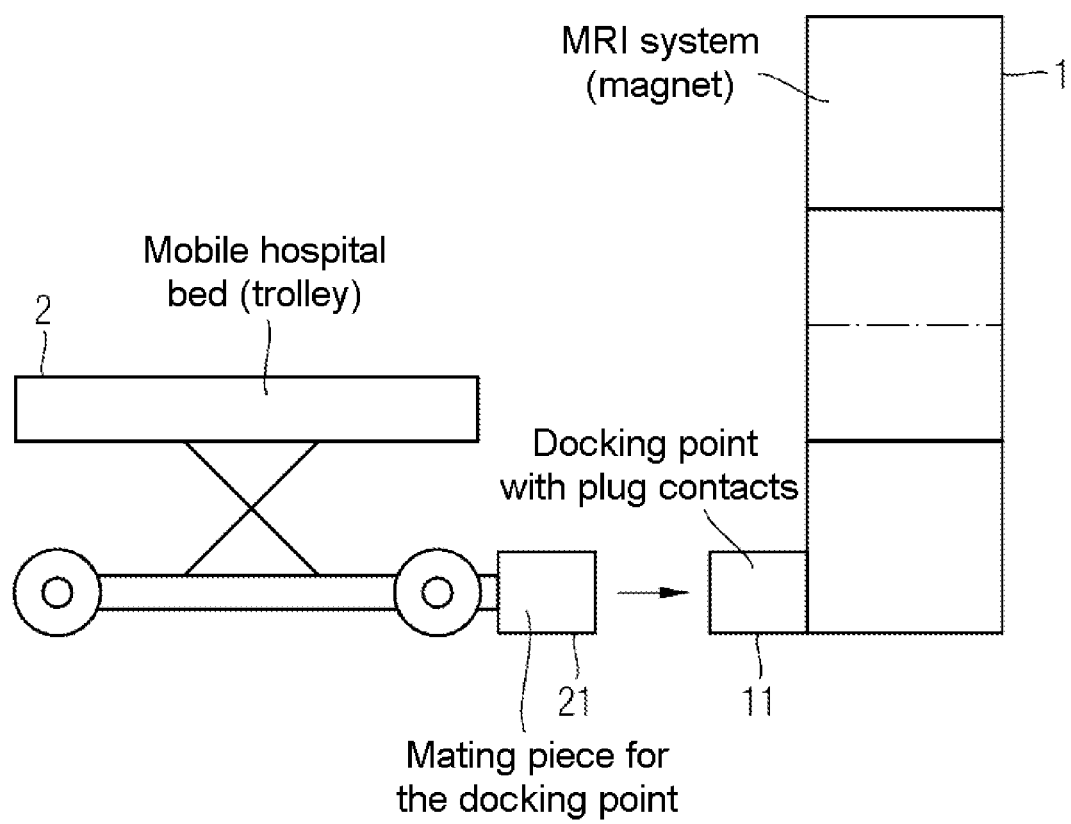
FIG. 1 illustrates the situation when a hospital bed is being docked to an MRI system.

This is schematically illustrated in FIG. 1, which shows an MRI system 1 having a docking interface with plug contacts 11 and a mobile hospital bed or a trolley 2 with a corresponding mating piece 21 for the docking point. The contacts that are to be established are the voltage supply for the bed itself, communications interfaces, safety signals and others, and also a large number of high-frequency lines (e.g., approximately 500 individual lines) for transmitting the high-frequency signals that are evaluated for producing the image. The background to this is that the various body coils (e.g., head coil, chest coil, arm coil etc.), in which the signals for producing the MR image that are relevant for measurement are produced, are attached to the patient and electrically connected to the bed during the treatment. From this connection point, the signals are transmitted via high-frequency cables, through the bed, via the docking point, to the imaging system.

On account of the large number of plug contacts, the force that the operator has to apply in order to dock or undock the table is very high. One or more of the present embodiments assist the operator during the docking and undocking processes in order to thereby reduce the operating forces to a reasonable level. In this case, the distance that is to be covered during docking with a high force may be only a few centimeters long.

In one or more of the present embodiments, only a minimum number of electrical contacts are produced between the bed and the system when manually docking a mobile hospital bed to an MRI system. The force that is to be applied by the operator for docking purposes is sufficiently low as a result. A DC motor in the bed is supplied with voltage by this leading contact. In addition, a mechanical connection between the bed and the system is established by a clip at the docking point. The clip engages in the table in the event of docking to a mating piece.

Figure 2:
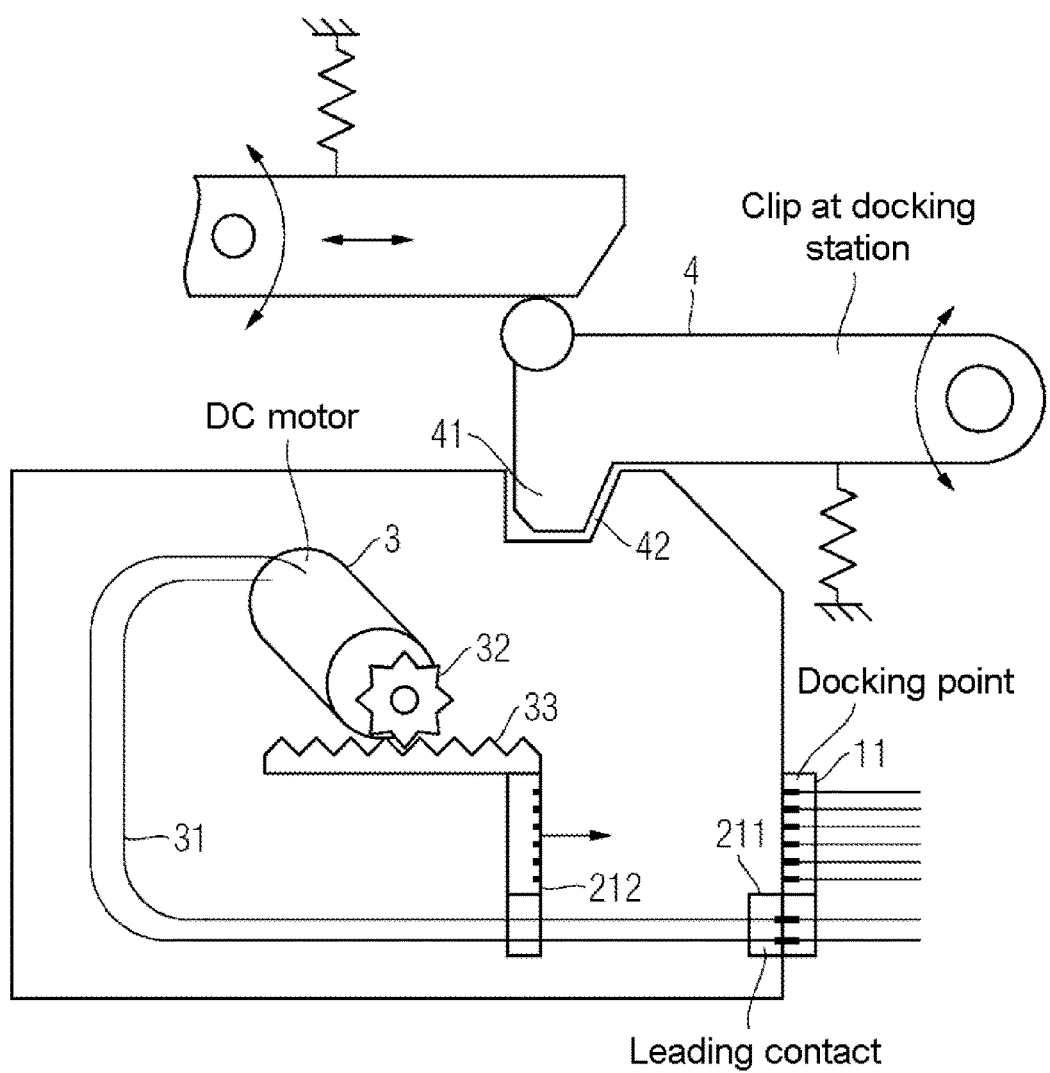
FIG. 2 shows one embodiment of a docking mechanism.

This is illustrated in detail in FIG. 2. The docking point 11 of the MRI device (not illustrated in the figure) is intended to be connected to the contact of the patient transportation apparatus. This contact of the hospital bed or transportation apparatus includes two parts (e.g., a leading contact 211 and a further contact 212). The further contact 212 is only connected to the docking point 11 in a second step. In FIG. 2, the leading contact between the docking point 11 and the contact element 211 is closed. As a result, a DC motor 3 that is arranged in the hospital bed may be supplied with power by the MRI device via this closed contact using the lines 31. The motor 3 is coupled to a gear wheel 32 that rotates together with the motor 3. As a result of the voltage being applied, the DC motor 3 is made to rotate and drives a toothed rack 33 via the gear wheel 32. The toothed rack 33 is, in turn, permanently connected to a mounting plate on which the remaining plug contacts 212 are mounted. The mounting plate is therefore moved in the direction of the docking point in a manner guided by linear guides until the plug contacts are fully connected. A large number of the plug contacts are therefore plugged or established without manual operating force, in a manner driven by the DC motor 3.

Figure 3:
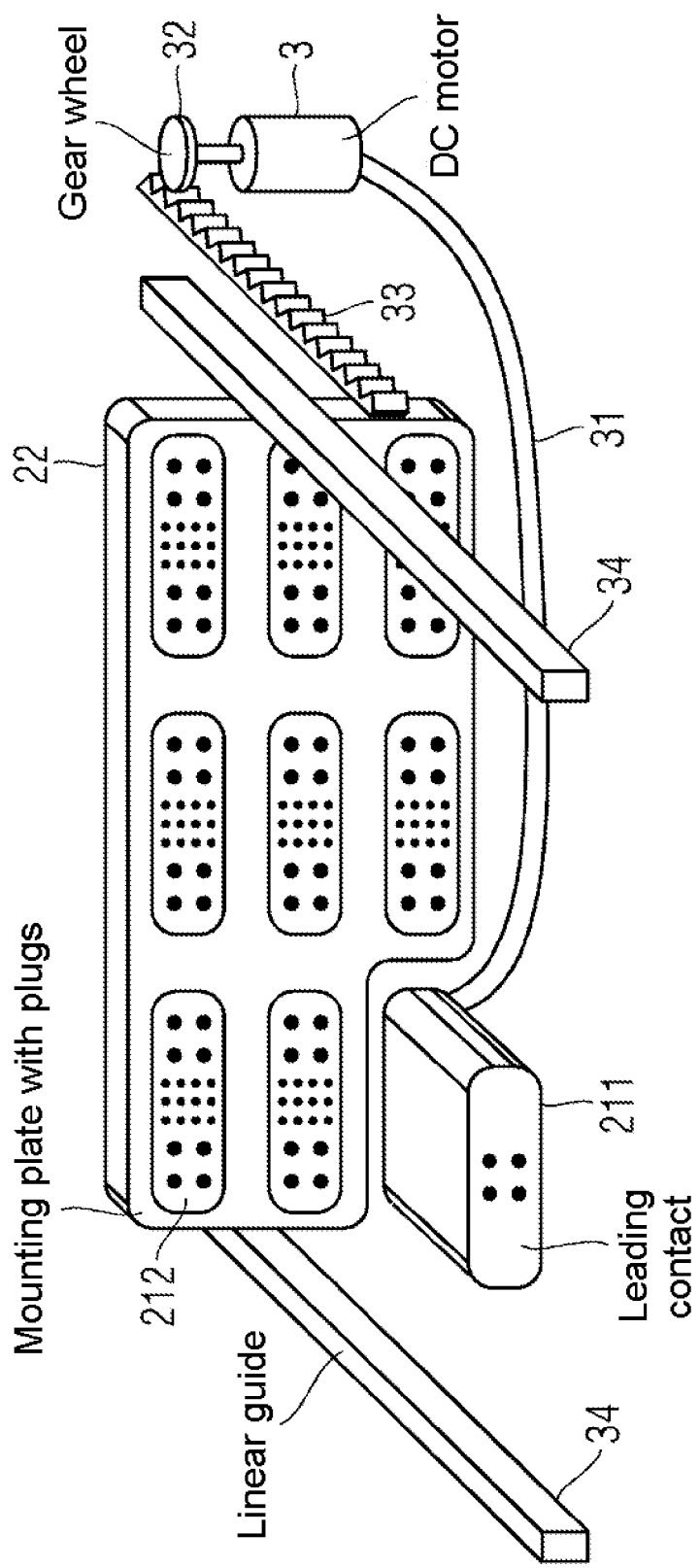
FIG. 3 shows a schematic plan view of one embodiment of a table-side docking interface from the direction of the MRI device.

FIG. 3 shows the table side of the docking mechanism even more clearly. A leading contact 211 that is connected to the DC motor 3 by lines 31 is provided, and therefore, the DC motor 3 may be supplied with power via these connections. The motor 3 is connected to the gear wheel 32 that drives the toothed rack 33. Further contacts 212 are mounted on a mounting plate 22 that is moved along linear guides 34 in order to make contact with the MRI device. The contacts may be divided into leading contacts 211 and contacts 212 that are to be established in a second step such that the minimum number of necessary leading contacts 211 is provided for supplying power to the DC motor 3. Using a minimum number of leading contacts 211 allows the first contact to be established with the lowest possible expenditure of force. In this case, a minimum number of contacts would be the number of contacts that is required for supplying power to the motor 3. This may also be a single contact.

Figure 4:
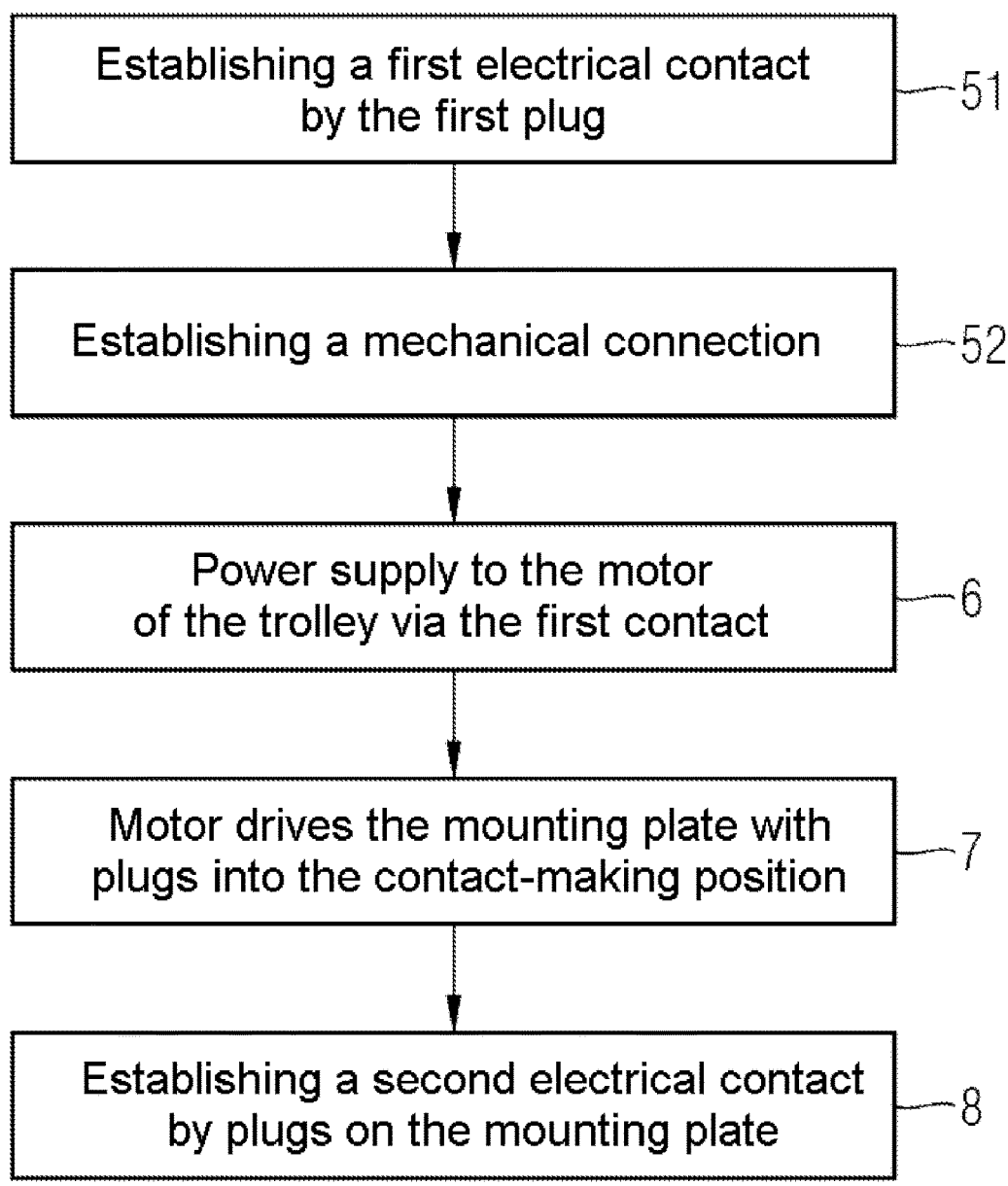
FIG. 4 shows a flowchart of one embodiment of a method.

FIG. 4 shows one embodiment of the procedure illustrated in the form of a flowchart. In act 51, a first electrical contact is established by a first plug. This may be performed at the same time as a mechanical connection is established, as is also indicated in FIG. 2. In FIG. 2, a clip 4 is provided at the docking point. The clip 4 is provided with a hook 41 that locks in a recess 42 in the hospital bed. Movement of the clip 4 and a locking arrangement of the clip 4 may also be triggered or initiated by establishing the first electrical contact. In FIG. 4, power is supplied to the motor of the trolley in act 6 after the first electrical contact is established. The mounting plate with plugs is moved into the contact-making position in act 7 in response to the supply of power. As a result, the second electrical contact is realized by plugs on the mounting plate. As a result of this, the contact-making process is completed.

One or more of the present embodiments are described based on docking a hospital bed to an MRI device. However, the concept according to the present embodiments is not restricted to this situation, but may be generally employed anywhere that a transportation apparatus is to be docked to a device that is supplied with power. In all of these cases, the device may be used as a power supply in order to complete the contact-making connection. This produces a two-step contact-making process, where the first part of the contact-making process is carried out manually, and the second part of the contact-making process is carried out in a manner assisted by motor. The power required for the motor is supplied via the first contact.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A transportation system configured to dock a transportation apparatus with a device from which power is supplied, the system comprising:
   the transportation apparatus comprising:
      a first contact element operable to establish a first contact with the device;
      a second contact element operable to establish a second contact with the device; and a first apparatus operated by a motor, the first apparatus operable to assist in establishing the second contact with the device; and the device comprising:
an interface operable to dock the transportation apparatus, the interface comprising a third contact element and a fourth contact element,
wherein the device is configured to transmit power to the transportation apparatus via the third contact element,
wherein the device is a medical diagnosis or therapy device,
wherein the interface is operable to receive a linear guide from the transportation apparatus to assist in establishing a second contact with the second contact element,
wherein power is provideable to the motor via the first contact element,
wherein the first apparatus is configured to assist in establishing the second contact by movement of the second contact element in a direction of the device, and
wherein the first apparatus comprises a linear guide operable to move the second contact element in the direction of the device.

2. The transportation apparatus of claim 1, wherein the second contact element is one second contact element of a plurality of second contact elements, the first apparatus operable to assist in establishing contact of the plurality of second contact elements with the device.

3. The transportation apparatus of claim 2, wherein the transportation apparatus is operable to assume a docking state in which the second contact element is extended in the direction of the device, and
wherein the transportation apparatus is operable to assume a movement state in which the second contact element is retracted.

4. The transportation apparatus of claim 3, wherein in the movement state of the transportation apparatus, the first contact element is arranged such that the first contact element is offset in relation to the second contact element such that during a docking process, the first contact element makes contact with the device without contact being made between the second contact element and the device.

5. The transportation apparatus of claim 1, wherein the transportation apparatus is operable to assume a docking state in which the second contact element is extended in the direction of the device, and
wherein the transportation apparatus is operable to assume a movement state in which the second contact element is retracted.

6. The transportation apparatus of claim 5, wherein in the movement state of the transportation apparatus, the first contact element is arranged such that the first contact element is offset in relation to the second contact element such that during a docking process, the first contact element makes contact with the device without contact being made between the second contact element and the device.

7. The transportation apparatus of claim 6, wherein the transportation apparatus is configured for a mechanical connection that is establishable in the movement state to the device.

8. The transportation apparatus of claim 7, wherein the establishment of the mechanical connection is initiatable by the first contact being established.

9. A device comprising:
an interface operable to dock a transportation apparatus, the interface comprising a first contact element and a second contact element,
wherein the device is configured to transmit power to the transportation apparatus via the first contact element,
wherein the device is a medical diagnosis or therapy device, and
wherein the interface is operable to receive a linear guide from the transportation apparatus to assist in establishing a second contact with the second contact element.

10. A system comprising:
a transportation apparatus configured to dock with a device to which power is supplied, the transportation apparatus comprising:
a first contact element operable to establish a first contact with the device;
a second contact element operable to establish a second contact with the device; and
a first apparatus operated by a motor, the first apparatus operable to assist in establishing the second contact with the device, wherein the first apparatus is configured to provide power to the motor with power from the first contact; and the device comprising:
an interface operable to dock the transportation apparatus, the interface comprising a first contact element and a second contact element,
wherein the device is configured to transmit power to the transportation apparatus via the first contact element,
wherein the device is a medical diagnosis or therapy device,
wherein the first apparatus is configured to assist in establishing the second contact by movement of the second contact element of the transportation apparatus in a direction of the device,
wherein the first apparatus comprises a linear guide operable to move the second contact element of the transportation apparatus in the direction of the device, and
wherein the interface is operable to receive the linear guide from the transportation apparatus to assist in establishing a second contact with the second contact element.

11. The system of claim 10, wherein the second contact element of the transportation apparatus is one second contact element of a plurality of second contact elements, the first apparatus operable to assist in establishing contact of the plurality of second contact elements with the device.

12. A method for establishing contact between a transportation apparatus and a device, the method comprising:
establishing a first contact by a first contact element of the transportation apparatus and a first contact element of the device;
supplying a motor of the transportation apparatus with power via the first contact; and
establishing a second contact between a second contact element of the transportation apparatus and a second contact element of the device, the establishing of the second contact being assisted by the motor,
wherein the second contact comprises a plurality of high-frequency lines for transmitting high-frequency signals from body coils electrically connected to the transportation apparatus.

13. The method of claim 12, further comprising moving, by the motor, the second contact element of the transportation apparatus toward the device for the purpose of making contact.

* * * * *